(12) United States Patent
Thornton et al.

(10) Patent No.: US 7,029,712 B1
(45) Date of Patent: Apr. 18, 2006

(54) TREATMENT FOR DRY EYE SYNDROME

(76) Inventors: Spencer P. Thornton, 5070 Villa Crest Dr., Nashville, TN (US) 37220; Ellen Troyer, 1 Mirada Rd., Colorado Springs, CO (US) 80906

( * ) Notice: Subject to any disclaimer, the term of this patent is extended or adjusted under 35 U.S.C. 154(b) by 0 days.

(21) Appl. No.: 10/521,067

(22) PCT Filed: Jul. 17, 2003

(86) PCT No.: PCT/US03/22297

§ 371 (c)(1),
(2), (4) Date: Jan. 11, 2005

(87) PCT Pub. No.: WO2004/006801

PCT Pub. Date: Jan. 22, 2004

Related U.S. Application Data

(60) Provisional application No. 60/396,222, filed on Jul. 17, 2002.

(51) Int. Cl.
| | |
|---|---|
| *A61K 35/78* | (2006.01) |
| *A61K 35/60* | (2006.01) |
| *A61K 33/06* | (2006.01) |
| *A61K 31/355* | (2006.01) |
| *A61K 31/07* | (2006.01) |

(52) U.S. Cl. .................. 424/756; 424/776; 424/523; 424/682; 424/697
(58) Field of Classification Search .................. None
See application file for complete search history.

(56) References Cited

U.S. PATENT DOCUMENTS

| 4,977,187 A * | 12/1990 | Horrobin .................... 514/560 |
| 6,093,706 A | 7/2000 | Zeligs |
| 6,316,465 B1 * | 11/2001 | Pershadsingh et al. ...... 514/310 |
| 6,506,412 B1 | 1/2003 | Troyer et al. |
| 6,537,581 B1 | 3/2003 | Tao |
| 6,585,987 B1 | 7/2003 | Fransoni |
| 2002/0009505 A1 * | 1/2002 | Tao ............................ 424/725 |
| 2002/0128191 A1 | 9/2002 | Scannon |
| 2002/0188024 A1 * | 12/2002 | Chilton et al. .............. 514/560 |

FOREIGN PATENT DOCUMENTS

| JP | 08040925 | * | 2/1996 |

OTHER PUBLICATIONS

Biswas et al. Phytotherapy Res. 2001. vol. 15, No. 7, pp. 618-620, EMBASE Abstract enclosed.*

* cited by examiner

*Primary Examiner*—Christopher R. Tate
(74) *Attorney, Agent, or Firm*—Sara A. Centioni; Michael A. Mann; Nexsen Pruet, LLC

(57) ABSTRACT

A novel formulation for the treatment of the many underlying inflammatory processes that cause dry eye syndrome. In particular, the formulation, which is orally administered includes the optimal blend of omega-3 and omega-6 essential fatty acids, and nutrient cofactors necessary to enhance the metabolic conversion associated with the tear-specific series E-one anti-inflammatory prostaglandin (PGE1). As used herein, the term "nutrient cofactor" refers to a compound that supports and enhances the conversion of linoleic acid to gamma-linolenic acid. Additionally, the formulation inhibits the production of pro-inflammatory compounds, as well as the growth of viral and bacterial pathogens of the three-layer tear film.

20 Claims, 1 Drawing Sheet

TREATMENT FOR DRY EYE SYNDROME

This application claims benefit of application Ser. No. 60/396,222 filed Jul. 17, 2003.

FIELD OF THE INVENTION

The present invention relates generally to the treatment of eye disorders, and, in particular, to an orally administered treatment for dry eye syndrome.

BACKGROUND OF THE INVENTION

Sufficient lubricating tears are critical to good eye health. Because tears provide the same functions for the cornea of the eye that the blood provides for the body, any abnormalities in tear production can results in eye disorders. One such disorder is dry eye syndrome. Dry eye syndrome, commonly referred to as "dry eyes," is a prevalent eye condition affecting approximately 20 million Americans. Specifically, dry eye syndrome is a disorder resulting generally from any abnormality in the tear production process, such as decreased tear production, excessive tear evaporation, or an abnormality in mucin or lipid component of the tear film that covers the normal ocular surface.

Although dry eye syndrome may have many different etiologies, the common denominator in all cases of dry eye is that it involves changes in the ocular surface due to alterations in the quality or quantity of tears. To understand the causes of dry eye syndrome, therefore, it is also important to understand the basics of tear production. The action of tears takes place in the three layers of the tear film. The mucin or mucus layer is the closest layer to the corneal epithelium. It is produced by the conjuctival goblet cells, and is absorbed by the corneal surface glycoproteins, creating a hydrophilic surface. Mucin deficiency, or mucopolysaccharide abnormalities, can lead to poor wetting or glycation of the corneal surface with subsequent desiccation and epithelial damage, even in the presence of adequate aqueous tear production. The aqueous layer, which floats on the mucin layer, is secreted by the lacrimal gland and incorporates all water-soluble components of the tear film. Further, the aqueous layer makes up 90% of the tear film's thickness. The significance of the aqueous layer is that it provides moisture and supplies oxygen and important nutrients to the cornea of the eye. Finally, on the outside of the aqueous layer is the lipid layer. The lipid or oil layer is produced by the meibomian glands with contributions from the glands of Zeis and Moll of the eye lids. The secretion of the lipid layer is an oily material, which is fluid at body temperature and retards the evaporation of the aqueous layer and lowers surface tension, thereby allowing the tear-film to adhere to the eye's surface. Androgen receptors are located in both the lacrimal and meibomian glands. A decrease in circulating androgen hormones can result in loss of the oil layer, which exacerbates the evaporative tear loss.

The ocular surface is bathed in tears that provide nutrients, lubrication, and information about chemical regulators to the cells of the corneal and conjunctiva. Tears are needed to maintain the normal ocular surface as well as to repair injury and surgical trauma. The blink reflex renews the tear film by delivering aqueous and lipid to the tear film and sweeping away debris. The normal blink interval is about 5 seconds under normal conditions. The tear film is typically stable for about 10 seconds. Tears are normally evaporated or forced out through the nasolacrimal ducts in the inner corner of the eyes on blinking.

Optimum ocular functioning requires essential fatty acids (EFAs). Because EFAs cannot be synthesized by the human body, they must be obtained from the diet. In particular, the omega-6 essential fatty acid, linoleic acid, is significant to dry eye syndrome. The body converts linoleic acid into series one prostaglandins (PGE1) by first converting it into gamma-linolenic acid (GLA), next into dihomo-gamma-linolenic acid, and finally into PGE1. PGE1 is important for lacrimal and salivary gland secretion and for T cell function. T cells are an essential element of the body's immune system, and the disruption of their functioning can contribute to the onset of diseases causing dry eye syndrome.

It is also important in the formation of PGE1 that the omega-6 essential fatty acids be in balance with omega-3 fatty acids. Omega-3 fatty acids help to prevent the metabolism of omega-6 fatty acids into pro-inflammatory compounds, thereby further enhancing the formation of PGE1. A disruption in this overall process is also believed to be an underlying cause of dry eye syndrome.

The typical symptoms of the dry eye syndrome include dryness, grittiness, irritation, difficulty reading for long periods of time, burning, and even the apparent contradiction of excessive tearing or watering. In extreme cases of dry eye, patients may become unusually sensitive to light, experience severe eye pain, and start to notice diminished vision. Successful treatment may be needed to avoid permanent damage.

These symptoms can result from many different causes of dry eye syndrome. Like most eye conditions, dry eye syndrome is often related to health conditions in the rest of the body, including dryness of other mucus membranes such as those located in the mount, vagina, and joints. Dry eye syndrome can also be a sign of digestive imbalances or of more serious systemic autoimmune diseases, such as rheumatoid arthritis, Sjogrens syndrome or lupus erthematosus. Other disorders, such as diabetes, glaucoma, thyroid disease, and blepharitis are also believed to be related to dry eye syndrome.

The causes of dry syndrome can be categorized based on which area or layer of the tear film is affected. Lubricant deficient dry eye encompasses disorders of the mucin layer and goblet cells. These disorders typically arise from vitamin A deficiency, protein malnutrition, conjunctival shrinkage, viral infections, thermal damage, irradiation damage, chemical injury, chemical preservatives, allergic conjunctivitis, and an increase in tear film osmolarity from lipid or aqueous dysfunction.

Aqueous tear-deficient dry eye encompasses disorders of the aqueous layer of the tear film. Tear deficient dry eye involves a decrease in the output of the lacrimal glands producing aqueous tears. This category can be further subdivided into Sjogrens-associated and non-Sjogrens-associated dry eye. Evidence exists that indicates that dry eye of both the Sjogrens and non-Sjogrens types has an inflammatory component that is an important feature in the pathogenesis of ocular surface disease. Sjogrens syndrome involves systems other than the eye including dry mouth, arthralgia, rheumatoid arthritis, and scleroderma. Non-Sjogrens aqueous deficiency, on the other hand, may be caused by age related atrophy of the lacrimal glands. The normal aging of tear glands, for example, can result in dryness, because tear volume decreases from age 18 as much as 60% by age 65. Further causes include isolated KCS, pharmaceuticals, menopause, noxious agents, damage to the lacrimal gland, and chronic viral infection.

Evaporative dry eye encompasses disorders of the lipid layer. Evaporative dry eye is characterized by excessive evaporative loss of tears from the ocular surface. The form most commonly encountered in clinical practice is meibomian gland dysfunction, which is characterized by a blockage of the mebomian glands and qualitative changes in the nature of their oily secretion. In normal eyes, lipids from the meibomian glands, and to a lesser extent the Moll and Zeiss glands, retard the evaporation of tears. Changes in the quality or quantity of tear lipids diminish the ability of the lipid layer to slow evaporation and maintain the integrity of the tear film. Both animal and human studies suggest that the pathogenesis of dysfunction of the lacrimal and meibomian glands may be linked. As is the case with aqueous tear-deficient dry eye, surface inflammation is a feature of evaporative dry eye and may play a role in both pathogenesis and symptomatology. Common causes for evaporative dry eye lipid layer disorders are aging, meibomianitis, and environmental conditions, such as the "sick office" syndrome, dry and/or windy climate, pollutants, and air conditioning. Computer use can also cause dry eye, as most people blink less frequently (about 7 times per minute vs. a normal rate of around 22 times/minute) that leads to increased evaporation along with fatigue and eye-strain associated with staring at a computer monitor.

It has now been clearly shown that a neural feedback mechanism links nerve endings on the ocular surface to the lacrimal glands. In response to neural stimulation, the lacrimal glands secrete a variety of components, including a number of small natural antibiotic proteins, like lactoferrin, an iron-binding protein released by neutrophils, and the neurotransmitter, acetylcholine which all play a significant role in controlling the turnover of epithelial cells on the corneal and conjunctival surfaces. The ocular surface nerve endings and the neural pathway are also important to the maintenance of a healthy ocular surface and the eye's ability to respond to injury.

Accordingly, the disruption of nerve endings on the ocular surface is also believed to cause dry eye syndrome. An example of this type of disruption occurs as a result of LASIK surgery. In LASIK surgery, up to 70% of the superficial corneal nerve endings are severed during flap creation. LASIK also introduces the following factors that can disrupt the sensory and autonomic neural connections that unify and drive the tightly integrated ocular surface/lacrimal/meibomian gland system: lid damage caused by the speculum, surgical induced fee radical production, decreased tear production, depressed corneal and conjunctival sensation, abnormal tear clearance, increase of inflammatory factors on ocular surface, and exacerbation of pre-operative, possibly sub clinical, dry eye.

Inflammation of the ocular surface may also disturb the nerve endings, which in turn would disrupt the neural feedback mechanism and adversely affect tear production and cellular renewal. Sensation plays a critical role in initiating blink, as well. With compromised sensation, the blink rate can slow to the point where the tear film breaks up before the next blink can reconstitute it. The resultant absence of tear film will expose the epithelial surface to drying, mechanical damage, and the release of agonal chemicals from within the cells. This result initiates an inflammatory process. Even minimal levels of dry eye will result in a low-level ocular surface inflammatory component. If left untreated, smoldering inflammation can cause damage over time and increase susceptibility to bacterial conjunctivitis and viral conjunctivitis.

Most physicians recognize the underlying inflammatory process that is a part of dry eye in general and post-LASIK and other surgical induced dry eye. One cannot cut into tissue without causing the release of pro-inflammatory mediators and the diffusion of inflammatory cells to the incision. Proper blinking is necessary to distribute the top oily layer of the tear film. Surgery causes an alteration in the ability of the lid and tear film to protect the ocular surface. As a result, epithelial cells die at a greater rate and release chemicals, which cause damage and inflammation.

Additional causes of dry eye syndrome include the following. Extended use of contact lens can result in dry eye from corneal oxygen and nutrient deficiency. Protein build-up on contact lens can produce a breeding ground for bacterial growth and surface roughness, further contributing to inflammatory changes. Also, medications such as antibiotics, blood pressure medications, antidepressants, diuretics, over-the-counter vasoconstrictors, antihistamines, birth control pills, appetite suppressants, and ulcer medications, refractive surgery, autoimmune diseases and disorders such as those mentioned above, hormonal changes, and nutritional deficiencies can cause disruption in the tear production and retention process.

The conventional treatment for dry eyes involves treating the symptoms rather than the cause. For example, artificial tears and ocular lubricants are a common treatment. Although artificial tears may provide temporary relief, they merely palliate the symptoms. Furthermore, the preservatives used in the artificial tears can actually aggravate the condition, and can even kill corneal cells. Artificial tears that promise to "get the red out" actually reduce circulation in the eye by vessel constriction, decreasing production of the tear film, and worse, eventually make the eyes drier. The "rebound" dilation of surface vessels further contributes to the inflammatory response.

Another form of treatment is punctal occlusion. Punctal occlusion is a procedure used to help dry eye patients by closing the tear drainage canals with silicone plugs, which keep most of the fluid from draining away from the surface of the eye. This may provide long-term relief.

Thus far, there have been few approaches to the treatment of dry eye disorders that have been effective in addressing all the issues regarding dry eye syndrome. The present applicant previously developed a formulation, which is described in the specification of U.S. Pat. No. 6,506,412 and sold under the trademark HYDROEYE®, for treating the underlying inflammatory processes that cause dry eye syndrome. However, the HYDROEYE® treatment focused only on the production of the anti-inflammatory PGE1 and mucin. Although inflammation is still the main concern in dry eye syndrome, site-specific anti-inflammatory prostaglandins only address part of the dry eye inflammatory process. For example, the formulation did not address the inhibition of pro-inflammatory compounds, such as PGE2 and Interleukin-1. Further, the formulation did not address the inhibition of the growth of viral and bacterial pathogens in the three-layer tear film through the production of lactoferrin, which is a natural antibiotic.

Accordingly, there remains a need for an improved formulation that addresses a wider range of the underlying inflammatory processes that cause dry eye syndrome.

SUMMARY OF THE INVENTION

According to its major aspects and briefly recited, the present invention is a novel formulation for the treatment of the many underlying inflammatory processes that cause dry eye syndrome. In particular, the formulation, which is orally administered includes the optimal blend of omega-3 and omega-6 essential fatty acids, and nutrient cofactors necessary to enhance the metabolic conversion associated with the tear-specific series E-one anti-inflammatory prostaglandin (PGE1). As used herein the term "nutrient cofactor" refers to a compound that supports and enhances the conversion of linoleic acid to gamma-linolenic acid. Additionally, the present formulation inhibits the production of pro-inflammatory compounds, as well as the growth of viral and bacterial pathogens of the three-layer tear film.

In a first embodiment, the formulation includes the following compounds or ingredients: 1) black currant seed oil, as a source of omega-3 and omega-6 essential fatty acids (EFAs), as well as gamma-linolenic-acid (GLA); 2) cod liver oil, as a source of omega-3 fatty acid, docosahexaeonic acid (DHA) and eicosapentaenoic acid (EPA); 3) vitamin E, as a mixture of d-alpha tocopherol and dl-alpha tocopherol, containing gamma tocopherol; 4) vitamin A, as retinal palmitate; 5) vitamin B6, as pyridoxal 5-phosphate; 6) magnesium, as magnesium sulfate; 7) vitamin C, as calcium ascorbate and ascorbic acid; 8) curcumin, as turmeric extract; 9) lactoferrin; and 10) mucin complex, as mucopolysaccharides.

In a second embodiment, any or all of the following ingredients are combined with the above-described formulation to impart particular features to the formulation: 1) L-carnitine; 2) DHEA (dehydroepiandrosterone); and 3) beta-glucan.

A unique feature of the present invention is the use of vitamin E in proper combination with the other components of the formulation. Vitamin E is an important regulator of prostaglandin E2 (PGE2), which plays a key role in inflammation and diseases associated with inflammation. Specifically, vitamin E inhibits cyclooxygenase-2 (COX-2) enzyme activity that promotes inflammatory response by catalyzing the synthesis of PGE2. Further, vitamin E enhances the T-cell function needed to inhibit the production of the pro-inflammatory Interleukin-1, which is responsible for inhibiting lacrimal aqueous secretion. Finally, vitamin stabilizes and prevents the oxidation of the omega-3 and omega-6 EFAs that are needed to generate anti-inflammatory PGE1.

Another feature of the present invention is the use of curcumin in combination with the other components of the formulation. Curcumin inhibits the expression and activity of the COX-2 enzyme involved in the production of inflammatory symptoms in the dry eye syndrome. As previously discussed, COX-2 is a necessary catalyst for the formation of the pro-inflammatory PGE2 and Interleukin-1. Specifically, curcumin is a natural COX-2 inhibitor with similar chemical properties to ibuprofens, such as those sold under the trademarks MOTRIN® and ADVIL®. The difference between these products and curcumin is that curcumin does not inhibit production of the COX-1 enzyme that is necessary to protect the stomach lining.

Yet another feature of the present invention is the use of APO-lactoferrin ("lactoferrin") in combination with the other components of the formulation. Lactoferrin, a glycoprotein present in milk, mucosal secretions and neutrophils, is a natural antibiotic that inhibits viral and bacterial infections through its ability to bind iron, and further balances other tear lipocalins (family of proteins that transport small hydrophobic molecules), which modulate the surface tension of the tear film and affect the comfort of the contact lens wearer. Because both bacteria and viruses depend on iron to grow, the inclusion of lactoferrin, which binds iron, helps to starve and inhibit these infections. Tear lipocalins (TLs) are the major lipid-binding protein in tears, and are able to increase the surface pressure of aqueous layer by scavenging lipids from hydrophobic surfaces and delivering them to the aqueous phase of the tear film. By introducing lactoferrin to the eye, the formulation helps to stimulate additional production of lactoferrin by the body. Without such an addition of lactoferrin, the production of lactoferrin by the body remains dependent on the gamma-linolenic-acid metabolite prostaglandins to signal the neutrophils in the aqueous and lipid layers of the tear film to produce lactoferrin.

Still another feature of the present invention is the use of L-carnitine in combination with the other components of the formulation. L-carnitine is an amino acid that serves as a cellular nutrient transport delivery medium for the movement the EFAs across the mitochondria.

The use of DHEA in combination with the other components of the formulation is yet another feature of the present invention. DHEA plays an important role in supporting lacrimal gland secretory function and increasing beta-andrenergic receptor binding sites. As hormone loss is believed to be a contributing factor to dry eye syndrome, the addition of hormones to the formulation enhances the effectiveness of the dry eye treatment.

Still another feature of the present invention is the use of beta-glucan in combination with the other components of the formulation. Beta-glucan acts as an immune system modulator and potentiator of the macrophage receptor sites by helping to modulate the T-cell/B-cell ratio. Further, beta-glucan reduces the production of Interleukin-1, a metabolite of the pro-inflammatory PGE2. Finally, beta-glucan enhances the immune response production of secretory IgA (protein immunoglobulin A) and IgE (protein immunoglobulin E), thereby inhibiting the binding of microorganisms to mucosal surfaces and inhibiting mast cell histamine mediated inflammatory response in the allergic dry eye.

Yet another feature of the present invention is the use of a synergistic blend of specific antioxidant components that stimulate and support normal functioning of oil and mucin secreting glands of the eyes a periorbita. This synergistic blend provides a means of restoring normal oil, mucous and tear secretions of the eye to relieve the condition of dry eye syndrome.

Still another feature of the present invention is the use of lubricant enhancing elements that are administered orally. A dietary nutritional supplement is administered to stimulate the natural production of lubricants as opposed to the use of superficial treatments for the symptoms of dry eye by administration of topical lubricants (eye drops).

Another feature of the present invention is the use a formulation for restoring normal lubrication to parts of the body affected by the nutritional deficiency of oil and mucin secreting glands, including, but not limited to, the mouth, vagina, joints and synovia.

Still another feature of the present invention is the use of formulation for relieving chronic inflammatory changes of the eye due to lack of specific anti-inflammatory components in the lacrimal and oil gland secretions.

Yet another feature of the present invention is the use of a synergistic blend of components in a stable, slowly oxidizable form for more assured potency.

Still another feature of the present invention is the use of both blandualr stimulants and anti-inflammatory components in one orally administered formulation.

Another feature of the present invention is the use of an immune system modulator to reduce the production of Interleukin 1 (IL-1), a metabolite of the pro-inflammatory PGE2, thereby lessening the need for potentially dangerous corticosteroids, which are now commonly used to reduce the IL-1 inflammatory process in the dry eye patient.

Still another feature of the present invention is the use of a treatment for dry eye syndrome by physiologic rather than pharmacologic means.

Other features and advantages of the present invention will be apparent to those skilled in the art from a careful reading of the Detailed Description of the Preferred Embodiment presented below and accompanied by the drawing.

DETAILED DESCRIPTION OF THE PREFERRED EMBODIMENTS

Figure 1:
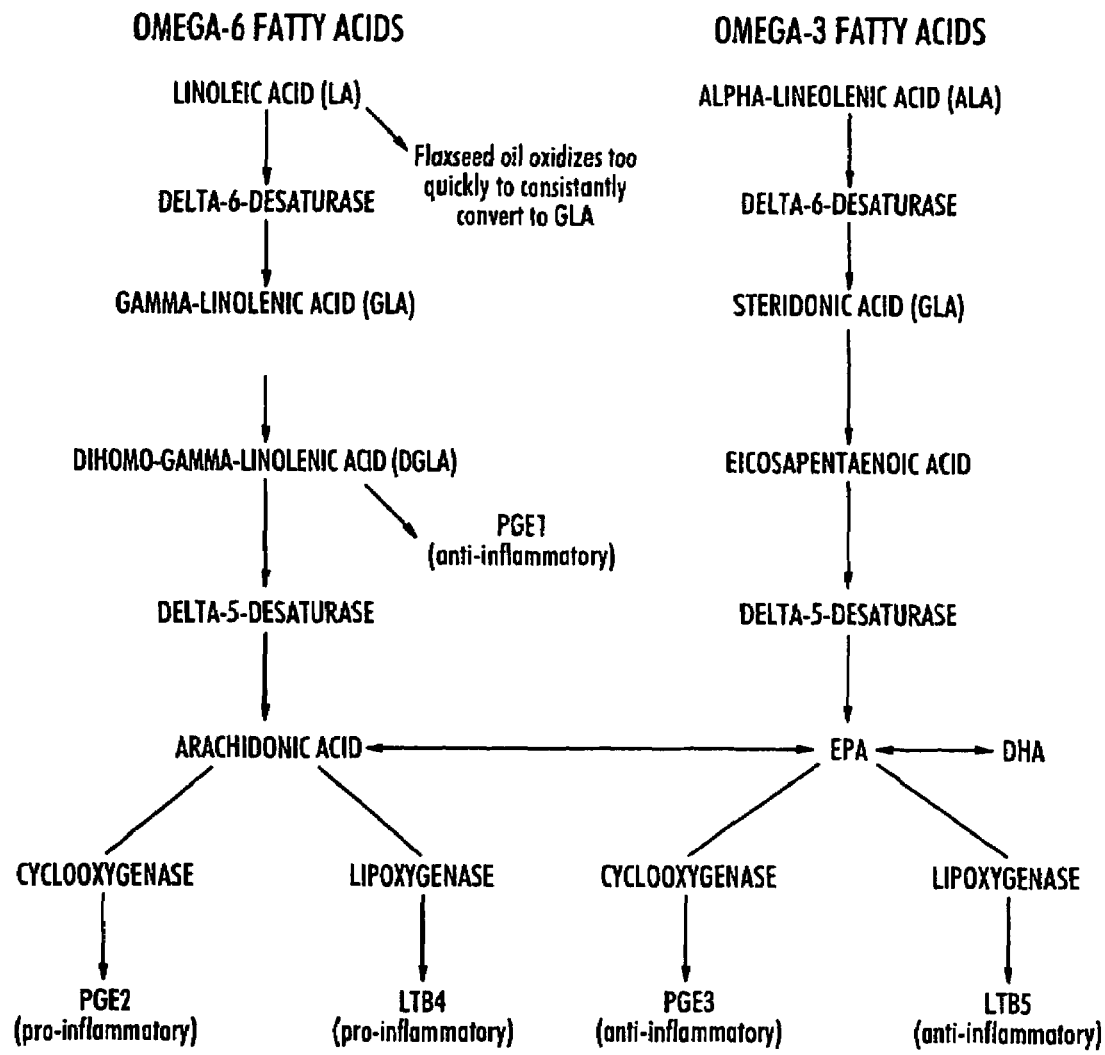
FIG. 1 is a schematic view of the metabolic pathways of omega-3 and omega-6 essential fatty acids according to a preferred embodiment of the present invention.

The present invention is an improved formulation for the treatment of the underlying inflammatory processes that cause dry eye syndrome. Through the oral administration of a blend of omega-3 and omega-6 essential fatty acids, and nutrient cofactors necessary to enhance the metabolic conversion associated with the tear-specific series E-one anti-inflammatory prostaglandin (PGE1), the root causes of dry eye syndrome are addressed. Additionally, the formulation inhibits the production of pro-inflammatory compounds, as well as the growth of viral and bacterial pathogens of the three-layer tear film. Although this particular formulation is described in connection with the treatment of human dry eye syndrome, it is also intended that the formulation and could also be used for the treatment of dry eye syndrome among various animals, such as dogs. [It is known that various animals having, for the most part, a similar physiology of the eye to the human eye also suffer from dry eye syndrome. Accordingly, the formulation of the present invention is also effective at treating dry eye syndrome among these various animals. Although, the effective amounts needed for the treatment vary between humans and animals, one skilled in the art can determine the differences in the effective amounts based on the particular size of the animals.]

In a first preferred embodiment, the formulation includes the following components along with the preferred ranges of amounts for each component:

Vitamin A (as retinyl palmitate) 1000 IU (or a range of 500 IU to 1600 IU)
Vitamin C 100 mg (or a range of 30 mg to 400 mg) (as Calcium ascorbate and Ascorbyl Palmitate)
Vitamin E (as mixed tocopherols oil) 32 IU (or a range of 10 IU to 200 IU)
Vitamin B6 (as pyridoxal-5-phosphate) 8 mg (or a range of 4 mg to 30 mg)
Magnesium (as magnesium sulfate) 20 mg (or a range of 10 mg to 200 mg)
Black currant seed oil 00 mg (or a range of 400 to 2500 mg)
Cod liver oil 2 mg (or a range of 1 mg to 7 mg)
Mucopolysaccharides (mucin complex) 250 mg (or a range of 50 mg to 400 mg)
Turmeric (*Curcuma longa*) extract (root) 100 mg (or a range of 20 mg to 300 mg)
Lactoferrin 10 mg (or a range of 5 mg to 200 mg)

In a second preferred embodiment, other components can be included to impart additional features to the formulation. Specifically, the compents L-carnitine, DHEA, and beta-glucan can be included into the above-described formulation either in combination or separately. The following is a list of the preferred ranges of these additional components that are included in combination with the above-described formulation:

L-carnitine 100 mg (or a range of 10 mg to 1000 mg)
DHEA 10 mg (or a range of 1 mg to 100 mg)
beta-glucan 100 mg (or a range of 10 mg to 1000 mg)

Although varying amounts of each component are contemplated by the present invention, the listed ranges are the approximate preferred ranges based on the necessary functions of each component in the treatment of dry eye syndrome. The formulation as described is preferably administered orally to a patient in a capsule form twice daily as a dietary supplement, wherein the patient takes two capsules with a morning meal and two capsules with an evening meal.

In order to understand the mechanism of action of the above described formulation, it is important to also understand the metabolic pathways of two of the key components of the formulation: omega-3 and omega-6 essential fatty acids (EFAs). Accordingly, FIG. 1 illustrates these metabolic pathways. As shown, omega-6 fatty acids metabolize to the site-specific anti-inflammatory, series E1 prostaglandin (PGE1), which systemically supports proper tear function. The series E1 prostaglandins augment eicosanoid (specific white blood cells) levels and thereby relieves chronic inflammation, which is a systemic cause of dry eye syndrome. PGE1 is beneficial in inhibiting inflammation in all mucosal tissue, and it is a particularly efficacious anti-inflammatory in both tears and saliva. Not only does PGE1 reduce ocular surface inflammation, but also the inflammatory process associated with meibomitis and reduced lacrimal gland aqueous output.

Omega-6 fatty acids convert to PGE1 via the linoleic-acid (LA) to gamma-linolenic-acid (GLA) to dihomo-gamma-linolenic-acid (DGLA) to the series E-one prostaglandins (PGE1). To ensure this conversion to PGE1, the nutrient cofactors, vitamins A, C, B6, and magnesium were also included in the formulation. The delta-6-desaturase (D6D) enzyme necessary for this conversion is too easily disrupted by such agents as alcohol, aging, smoking, elevated cholesterol levels, viral infections, cardiovascular disease, hormonal fluctuations, sugar consumptions, chemical carcinogens, and environmental factors without these additional nutrient cofactors. Advantageously, these nutrient cofactors also modulate goblet cell production, lacrimal gland aqueous tear production, meibomian gland function, and neurotransmitter blink response.

However, the formation of PGE1 is only a portion of the dry eye inflammatory process needed to be addressed for effective treatment. For example, the production of pro-inflammatory compounds is also an underlying inflammatory process that needs to be inhibited for effective treatment of dry eye syndrome. As shown in FIG. 1, if PGE1 is not formed and DGLA is metabolized into arachidonic acid, pro-inflammatory compounds such as PGE2 and LTB4 (Leukotriene B4) are formed. Accordingly, the present invention blocks the formation of arachidonic acid with the addition of vitamin E gamma tocopherols, EPA (eicosapentaenoic acid) from cod liver oil, and curcumin. Additionally, anti-inflammatory compounds such as PGE3 and LTB5, which are produced downstream of the metabolic pathway of omega-3 fatty acids, further contribute to an enhanced treatment of dry eye syndrome.

The formulation further includes components that inhibit viral and bacterial infections that affect the tear film and contribute to dry eye syndrome. Specifically, the formulation includes apo-lactoferrin, which increases the aqueous level of iron binding proteins and helps to modulate the surface tension of the tear film.

The following discusses the components of the above described formulation and explains their respective functions in the treatment of dry eye syndome:

Black currant seed oil provides both linoleic acid and gamma-linolenic-acid (GLA) from omega-3 and omega-6 EFAs, which are the metabolic precursors to PGE1. Biochemically, black currant seed oil is the most stable source of linoleic acid. Furthermore, black currant seed oil contains 18% GLA, which converts to anti-inflammatory PGE1 with the aid of the other nutrient cofactors vitamins A, C, B6, and magnesium. Omega-3 fatty acid, omega-6 fatty acid and GLA together make up approximately 31% of black currant seed oil.

Cod liver oil, which is preferably pharmaceutical grade, provides the necessary omega-3 fatty acid, docosahexaeonic acid (DHA) to balance the black current seed oil omega-6s ratio for the consistent metabolism of the anti-inflammatory PGE1. To further insure the omega-6 downstream conversion to PGE1, DHA/EPA omega-3 fatty acids inhibit the delta-5-desaturase (D5D) enzymatic metabolic conversion to arachidonic acid (AA), which can convert to pro-inflammatory cyclooxygenase-2 (COX-2) and prostaglandin E2, as well as LTB4. Additionally, omega-3 serves as a metabolic gateway boost to the downstream conversion of the omega-3 to the anti-inflammatory compounds, PGE3 and LTB5. Other cold-water fish oils can be used, but cod liver oil is preferred.

Vitamin A, as retinal palmitate, in proper combination with the other components of the formulation helps stabilize delta-6-desaturase, which is necessary for the formation of PGE1. Vitamin A additionally regulates the proliferation of corneal epithelial cells and preserves goblet cells. It is also required for the synthesis of mucin glycoproteins in the eye. A deficiency of vitamin A can result in abnormal epithelial cells in the eyelids, lacrimal glands, and conjunctiva. Finally, vitamin A deficiency can also produce abnormalities of the precorneal tear film and tear glands, and induce the occurrence of dry eye syndrome.

Vitamin C, as ascorbic acid and fat-soluble absorbyl palmitate, also helps to stablize D6D, which is required for the downstream conversion of omega-6 linoleic acid to PGE1. Preferably, there is 50% ascorbic acid and 50% absorbyl palmitate in the vitamin C. Further, because of the extended half-life of the fat soluble vitamin C over water-soluble ascorbic acid, vitamin C consistently modulates PGE1 synthesis. The combination of vitamin C with the other components of the formulation also enhances the production of IgE concentrates in tears, the first line of basophil and mast cell defense against invading pathogens and allergens that frequently cause dry eye symptoms.

Vitamin B6, as pyridoxal-5-phosphate, is yet another necessary nutrient cofactor for the stabilization of D6D. Pyridoxal-5-phosphate is the active form of vitamin B6.

Magnesium, as magnesium sulfate having 20% magnesium, is another essential cofactor in the conversion of linoleic acid into GLA.

Mucin complex, or mucopolysaccarides, provides mucin glycoproteins for the maintenance of the mucin network layer in the tear film.

Vitamin E, as a mixture of d-alpha tocopherol and di-alpha tocopherol, containing gamma tocopherol, is an important regulator of prostaglandin E2 (PGE2), which plays a key role in inflammation and diseases associated with inflammation. Preferably, the vitamin E mixture contains an equal amount of both d-alpha tocopherol and dl-alpha tocopherol. Specifically, vitamin E inhibits cyclooxygenase-2 (COX-2) enzyme activity that promotes inflammatory response by catalyzing the synthesis of PGE2. Further, vitamin E enhances the T-cell function needed to inhibit the production of the pro-inflammatory Interleukin-1, which is responsible for inhibiting lacrimal aqueous secretion. Finally, vitamin E stabilizes and prevents the oxidation of the omega-3 and omega-6 EFAs that are needed to generate anti-inflammatory PGE1.

Apo-lactoferrin, a glycoprotein present in milk, mucosal secretions and neutrophils, inhibits viral and bacterial infections through its ability to bind iron, and further balances other tear lipocalins (family of proteins that transport small hydrophobic molecules), which modulate the surface tension of the tear film and affect the comfort of the contact lens wearer. Tear lipocalins (TLs) are the major lipid-binding protein in tears, and are able to increase the surface pressure of aqueous layer by scavenging lipids from hydrophobic surfaces and delivering them to the aqueous phase of the tear film.

L-carnitine is an amino acid that serves as a cellular nutrient transport delivery medium for the movement the EFAs across the mitochondria.

DHEA plays an important role in supporting lacrimal gland secretory function and increasing beta-andrenergic receptor binding sites.

Beta-glucan acts as an immune system modulator and potentiator of the macrophage receptor sites by helping to balance the T-cell/B-cell ratio. Further, beta-glucan reduces the production of Interleukin-1, a metabolite of the pro-inflammatory PGE2. Finally, beta-glucan enhances the immune response production of secretory IgA and IgE, which inhibits the binding of microorganisms to mucosal surfaces and inhibits mast cell histamine mediated inflammatory response in the allergic dry eye.

It will be apparent to those skilled in the art that many changes and substitutions can be made to the preferred embodiment herein described without departing from the spirit and scope of the present invention as defied by the appended claims.

What is claimed is:

1. A formulation for the oral treatment of dry eye syndrome, comprising:
   an effective amount of omega-3 fatty acid;
   an effective amount of omega-6 fatty acid;
   an effective amount of gamma-linolenic-acid;
   an effective amount of nutrient cofactors
   an effective amount of lactoferrin;
   an effective amount of mucin complex;
   an effective amount of vitamin E; and
   an effective amount of curcumin.

2. The formulation as recited in claim 1, further comprising an effective amount of DHEA.

3. The formulation as recited in claim 1, further comprising an effective amount of l-carnitine.

4. The formulation as recited in claim 1, further comprising an effective amount of beta-glucan.

5. The formulation as recited in claim 1, wherein said nutrient cofactors are selected from the group consisting of vitamin A, vitamin B6, vitamin C, magnesium, and any combination thereof.

6. The formulation as recited in claim 1, wherein said omega-3 fatty acid is provided by cod liver oil.

7. The formulation as recited in claim 1, wherein said omega-6 fatty acid is provided by black currant seed oil.

8. The formulation as recited in claim 1, wherein said gamma-linonlenic-acid is provided by black currant seed oil.

9. The formulation as recited in claim 1, wherein said vitamin E is a mixture.

10. The formulation as recited in claim 1, wherein said curcumin is provided by turmeric extract.

11. A formulation for the treatment of dry eye syndrome, comprising:
   black currant seed oil, in a range of 400 mg to 2500 mg;
   cod liver oil, in a range of 1 mg to 7 mg, wherein the ratio between said black currant seed oil to said cod liver oil is 400 mg/1 mg;
   vitamin A, in a range of 500 IU to 1600 IU;
   vitamin C, in a range of 30 mg to 400 mg;
   vitamin B6, in a range of 4 mg to 30 mg;
   lactoferrin, in a range of 5 mg to 400 mg;
   magnesium, in a range of 10 mg to 200 mg;
   mucin complex, in a range of 50 mg to 400 mg;
   vitamin E, in a range of 10 IU to 200 IU; and
   curcumin, in a range of 20 mg to 300 mg.

12. The formulation as recited in claim 11, further comprising DHEA, in a range of 1 mg to 100 mg.

13. The formulation as recited in claim 11, further comprising l-carnitine, in a range of 10 mg to 1000 mg.

14. The formulation as recited in claim 11, further comprising beta-glucan, 10 mg to 1000 mg.

15. The formulation as recited in claim 11, wherein said vitamin C is a blend of 50% calcium ascorbate and 50% ascorbyl palmitate.

16. The formulation as recited in claim 11, wherein said vitamin E is a mixture of 50% d-alpha tocopherol and 50% dl-alpha tocopherol containing gamma tocopherol.

17. A formulation for the treatment of dry eye syndrome, comprising:
   black currant seed oil, at least about 800 mg;
   cod liver oil, at least about 2 mg;
   vitamin A, at least about 1000 IU;
   vitamin C, at least about 100 mg;
   vitamin B6, at least about 8 mg;
   lactoferrin, at least about 10 mg;
   magnesium, at least about 20 mg;
   mucin complex, at least about 250 mg;
   vitamin E, at least about 32 IU; and
   curcumin, at least about 100 mg.

18. The formulation as recited in claim 17, further comprising DHEA, at least about 10 mg.

19. The formulation as recited in claim 17, further comprising l-carnitine, at least about 100 mg.

20. The formulation as recited in claim 17, further comprising beta-glucan, at least about 100 mg.

* * * * *

UNITED STATES PATENT AND TRADEMARK OFFICE
CERTIFICATE OF CORRECTION

PATENT NO. : 7,029,712 B1
APPLICATION NO. : 10/521067
DATED : April 18, 2006
INVENTOR(S) : Spencer P. Thornton and Ellen Troyer It is certified that error appears in the above-identified patent and that said Letters Patent is hereby corrected as shown below:

Title page,
Insert Item:

insert -Assignee: Biosyntrx, Inc., Lexington, South Carolina, United States

Column 7
Line 54, should read -- Black currant seed oil 800 mg-

Signed and Sealed this

Twenty-second Day of August, 2006

JON W. DUDAS
*Director of the United States Patent and Trademark Office*